(12) United States Patent
Baptista et al.

(10) Patent No.: US 8,876,907 B2
(45) Date of Patent: Nov. 4, 2014

(54) CEMENT PRESSURIZING GLENOID

(75) Inventors: Alexandre A. N. Baptista, Plantation, FL (US); Jeffrey Duncan Sander, Liberty Township, OH (US); Shawn Michael Kroll, Waldwick, NJ (US); Gerald Rosenberg, Mount Desert, ME (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 13/558,872

(22) Filed: Jul. 26, 2012

(65) Prior Publication Data

US 2014/0031945 A1 Jan. 30, 2014

(51) Int. Cl.
*A61F 2/40* (2006.01)
*A61F 2/30* (2006.01)
*A61F 2/46* (2006.01)

(52) U.S. Cl.
CPC ..... *A61F 2/4081* (2013.01); *A61F 2002/30822* (2013.01); *A61F 2002/30897* (2013.01); *A61F 2002/4631* (2013.01); *A61F 2002/30891* (2013.01)
USPC .................. 623/19.11; 623/19.13; 623/19.14

(58) Field of Classification Search
CPC ....................................... A61F 2/40
USPC ........................................ 623/18.11–20.36
See application file for complete search history.

(56) References Cited

U.S. PATENT DOCUMENTS

| | | | |
|---|---|---|---|
| 4,964,865 A | 10/1990 | Burkhead et al. | |
| 5,032,132 A | 7/1991 | Matsen, III et al. | |
| 5,080,673 A | 1/1992 | Burkhead et al. | |
| 5,573,448 A | 11/1996 | Nakazima et al. | |
| 5,593,448 A | 1/1997 | Dong | |
| 6,379,386 B1 | 4/2002 | Resch et al. | |
| 6,911,047 B2 | 6/2005 | Rockwood, Jr. et al. | |
| 7,753,959 B2 | 7/2010 | Berelsman et al. | |
| 2010/0228352 A1 | 9/2010 | Courtney, Jr. et al. | |
| 2010/0241235 A1 | 9/2010 | Basamania et al. | |
| 2011/0035013 A1 | 2/2011 | Winslow et al. | |
| 2011/0118846 A1* | 5/2011 | Katrana et al. | 623/19.13 |
| 2012/0130499 A1* | 5/2012 | Long | 623/19.11 |

FOREIGN PATENT DOCUMENTS

| | | |
|---|---|---|
| EP | 1136046 A2 | 9/2001 |
| EP | 1 323 395 A2 | 7/2003 |

OTHER PUBLICATIONS

Extended European Search Report for Application No. 13177866 dated Oct. 16, 2013.

* cited by examiner

*Primary Examiner* — Yashita Sharma
(74) *Attorney, Agent, or Firm* — Lerner, David, Littenberg, Krumholz & Mentlik, LLP

(57) ABSTRACT

A prosthetic glenoid component has a body having a concave bearing surface and a convex glenoid contacting surface. First and second pegs extend outwardly from adjacent respective first and second ends of the bone contacting surface of the body, the first and second pegs have portions with a first diameter at the bone contacting surface extending for a first length and a second diameter extending from the first diameter for a second length, the first diameter larger than the second diameter. A third peg extends outwardly from the bone contacting surface intermediate the first and second pegs. The third peg has a third diameter greater than the second diameter portion of the first and second pegs and a third length greater than the first length of the first diameter portion of the first and second pegs. The third length is less than the sum of the first and second lengths.

18 Claims, 7 Drawing Sheets

CEMENT PRESSURIZING GLENOID

BACKGROUND OF THE INVENTION

The present invention relates generally to prosthetic implants for reconstructing the shoulder joint. More specifically, the invention relates to a glenoid component for a shoulder prosthesis and a method for affixing the glenoid component to a scapula in an implant procedure.

The glenoid cavity is located on the upper external border of the scapula between the acromion process and the coracoid process on a boney formation known as the scapula head. The glenoid cavity is a shallow, pear shaped, articular surface whose longest diameter is in the proximal-distal direction. It is broader distally than proximally, and its apex is a slight impression, the supra-glenoid tubercle, to which is attached the long tendon of the biceps muscle. The cavity is covered with cartilage and its margins, slightly raised, give attachment to a fibro-cartilaginous structure, the glenoid ligament, by which its cavity is deepened. The glenoid cavity articulates with a large, rounded head at the proximal end of the humerus. The head is nearly hemispherical in form and is directed proximally and medially and slightly posteriorly. Its surface is smooth and coated with cartilage.

Multiple forces are applied to the glenoid cavity and are accounted for in designing a glenoid prosthesis. Typically, the glenoid resurfacing component is made of ultrahigh molecular weight polyethylene (UHMWPE) having a concave laterally facing articulating surface and a convex medial bone contacting surface, which may include multiple pegs. The pegs resist the various types of loading placed on the glenoid by the head portion of the humeral component allowing the glenoid component to offer a stable and secure articulating surface. Typically, the pegs are inserted into a hole bored in the glenoid cavity and are secured either by bone cement or by being press fit in the bores.

Typically, the medial surface of the glenoid component includes three to five pegs to stabilize and secure the glenoid component to the scapula. The glenoid components may offer one of two larger diameter pegs and multiple pegs especially on the distal medial surface of the glenoid component. The pegs on the glenoid component are located and oriented for placement within the scapula at locations where maximum amounts of natural bone are available for effective anchoring of the pegs and for minimal risk of deleterious bone perforation, and for managing moments exerted on the glenoid component as a result of the forces encountered during service. For more effective resistance to separation of the glenoid component from the scapula, the glenoid component typically employs a full complement of the fixation pegs combined with an overall curved affixation surface for resisting shear forces and rocking the glenoid on the scapula, while preserving existing natural bone at the implant site.

Typical glenoid components are shown in U.S. Pat. Nos. 4,964,865; 5,573,448; 6,379,386; and 6,911,047.

BRIEF SUMMARY OF THE INVENTION

The prosthetic glenoid component of the present invention has a body having a concave bearing surface and a convex glenoid contacting surface. The body has a first end and a second end with first and second pegs extending outwardly from adjacent the respective first and second ends of the bone contacting surface of the body. The first and second pegs have portions with a first diameter at the bone contacting surface extending for a first length and a second diameter extending from the first diameter for a second length, the first diameter being larger than the second diameter. A third peg extends outwardly from the bone contacting surface intermediate the first and second pegs. The third peg has a third diameter greater than the second diameter portion of the first and second pegs and a third length greater than the first length of the first diameter portion of the first and second pegs, the third length less than the sum of the lengths of the first and second peg portions.

The first and second diameters of the first and second peg portions are preferably equal.

The first and second pegs may have circumferential grooves formed around their first and second diameters and the pegs may also have longitudinally extending grooves.

The first, second, and third pegs each have a longitudinal central axis wherein the longitudinal axis of the first, second, and third pegs are all parallel. The first portion diameter of the first and second pegs is equal to the third diameter of the third peg.

The glenoid may further comprise a fourth peg extending outwardly of the bone contacting surface adjacent the first end of the bone contacting surface.

The first and fourth pegs have a central longitudinal axes which may be parallel and coplanar along a first plane.

The second and third pegs each have central longitudinal axis which are parallel and coplanar along a second plane which is perpendicular to the first plane. The axis of the first peg may also be parallel and coplanar with the longitudinal axis of the second and third pegs.

The invention also relates to a method for implanting a prosthetic component in a scapular glenoid cavity includes forming three bores in a glenoid cavity including a proximal first bore, a distal second bore, and a third bore intermediate the first and second bores.

A prosthetic glenoid component is provided for implantation in the glenoid cavity which has a body having a concave bearing surface, and a bone contacting surface having three pegs extending outwardly therefrom. A first proximal peg has a first length, a second distal peg has a second length, and a third peg intermediate the first and second pegs has a length shorter than the first and second pegs. The first and second pegs have a larger diameter first portion adjacent the glenoid bone contacting surface and a smaller diameter second portion adjacent a free end of the first and second pegs. The glenoid component is implanted by first inserting the smaller diameter second portion of the first and second pegs, respectively into the proximal first bore and the distal second bore. Thereafter the third peg is inserted into the third bore and lastly the large diameter first portion of the first and second pegs is inserted into the first and second bores.

The first, second, and third bores may be filled with bone cement prior to implanting the glenoid component. Each of the pegs may have recessed circumferential grooves for receiving the bone cement.

The larger portion of the first and second pegs and the first and second bores have diameters producing line to line contact therebetween or may overlap slightly to produce an interference fit.

The third peg and the central bore may also have diameters which produce line to line contact or an interference fit therebetween.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

BRIEF DESCRIPTION OF THE DRAWINGS

FIG. 10 showing the engagement of the central bore with the central peg just prior to the engagement of the larger diameter of the left-hand peg with the bore; and FIG. 11 showing the cement being pressurized in the respective bore by the larger diameter of the left-hand peg of FIG. 11 and the central (right-hand peg) of FIG. 11.

DETAILED DESCRIPTION

Figure 1:
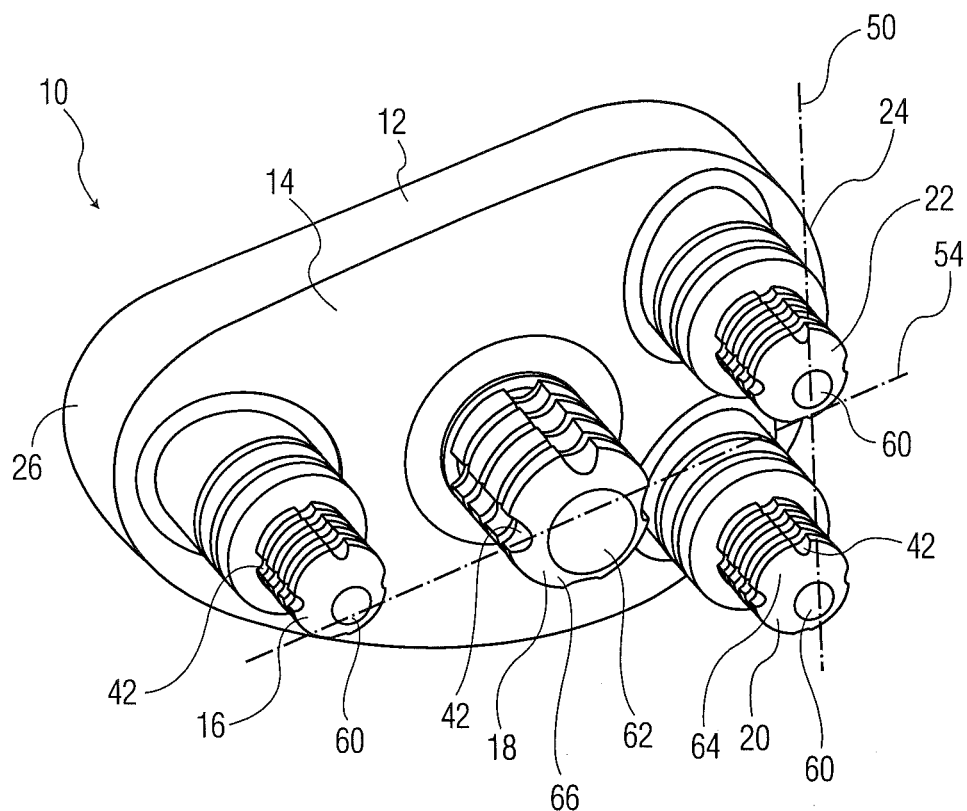
FIG. 1 is an isometric view of a glenoid component of the present invention viewed from a bone contacting or medial side.
Figure 2:
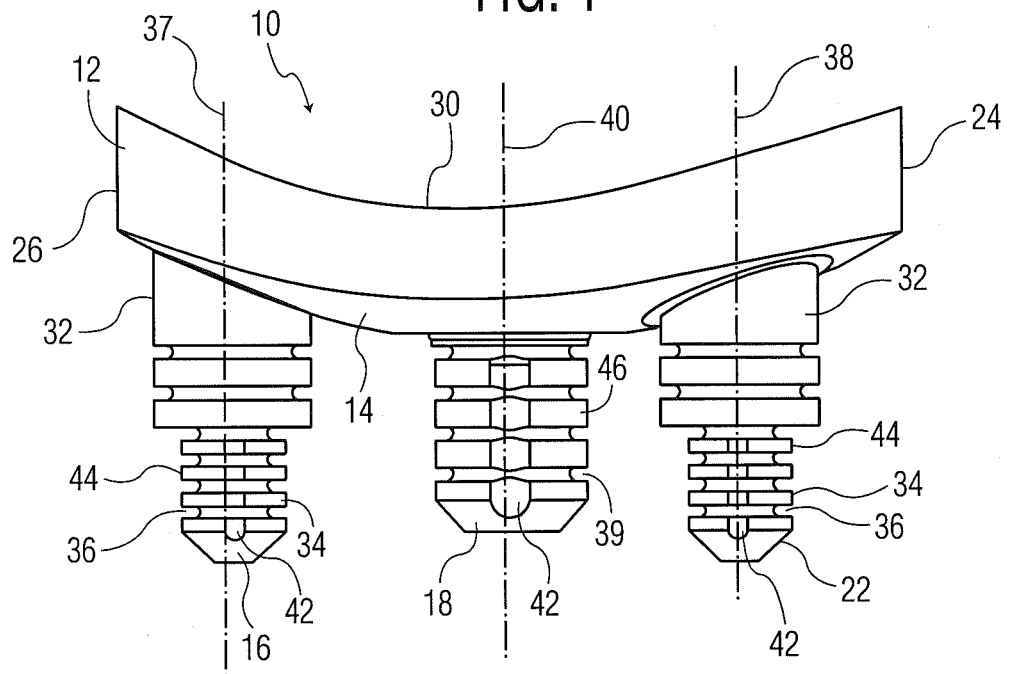
FIG. 2 is an elevation view of the glenoid component of FIG. 1.

Referring to FIGS. 1 and 2, there is shown an isometric view of a first embodiment of a glenoid component generally denoted as 10. This embodiment has a body 12 with a bone contacting surface 14 and has four pegs 16, 18, 20, and 22. During implantation on the scapula, body 12 has a distal or inferior end 24 and a proximal or superior end 26.

In the embodiment of glenoid component 10 shown in FIG. 1, there are two pegs 20 and 22 at distal end 24 and one peg a proximal or superior end 26. A central peg 18 is provided on the body. It should be noted that the scapula or glenoid cavity is prepared in a standard manner to create four bores corresponding in location to the four pegs 16, 18, 20 and 22 on the bone contacting surface 14 of glenoid component 10. Pegs 16, 20 and 22 have a central longitudinal axis 38 and peg 18 has a central longitudinal axis 40.

Referring to FIG. 2 can be seen at body 12 includes a bearing surface 30 which is designed to articulate against a prosthetic humeral head (not shown). From FIG. 2 it can also be seen that pegs 16 and 22 are identically shaped and extend away from the bone contacting surface a greater distance than central peg 18. As shown, pegs 16 and 22 include a first larger diameter portion 32 adjacent bone contacting surface 14 and a smaller diameter second portion 34 extending medially from an end of the larger first diameter portion 32. It should be noted that peg 22 is preferably also identical to pegs 16 and 20.

Since the glenoid component of FIGS. 1 and 2 is primarily designed for use with bone cement, the first and second portions 32 and 34 of pegs 16, 20, and 22 have surfaces with circumferentially extending grooves 36. As can be seen, multiple grooves 36 are spaced along each peg generally perpendicular to the central axis 38. Central peg 18 also includes a series of grooves 39 extending around the circumference thereof centered about axis 40 of peg 18 and generally perpendicular thereto. Peg 18 and portions 34 of pegs 16, 20, and 22 may include at least one axial groove 42 extending through each of the flanged portions 44 created by circumferential grooves 36 on pegs 16, 20, and 22 as well as flange 46 formed by grooves 39 on central peg 18. The purpose of the axial grooves 42 is to allow bone cement to move upwardly in the bores formed in the glenoid cavity upon insertion of the glenoid component 12 therein. Grooves 42 ensure that pressurized bone cement flows into the grooves 36 and 39 to ensure positive interlocking between the glenoid component 12 and the scapula. Any number of grooves can be used on pegs 16-22 so long as the flanges 44 and 46 are thick enough to resist deformation upon standard loads being applied to the glenoid component during use.

Figure 3:
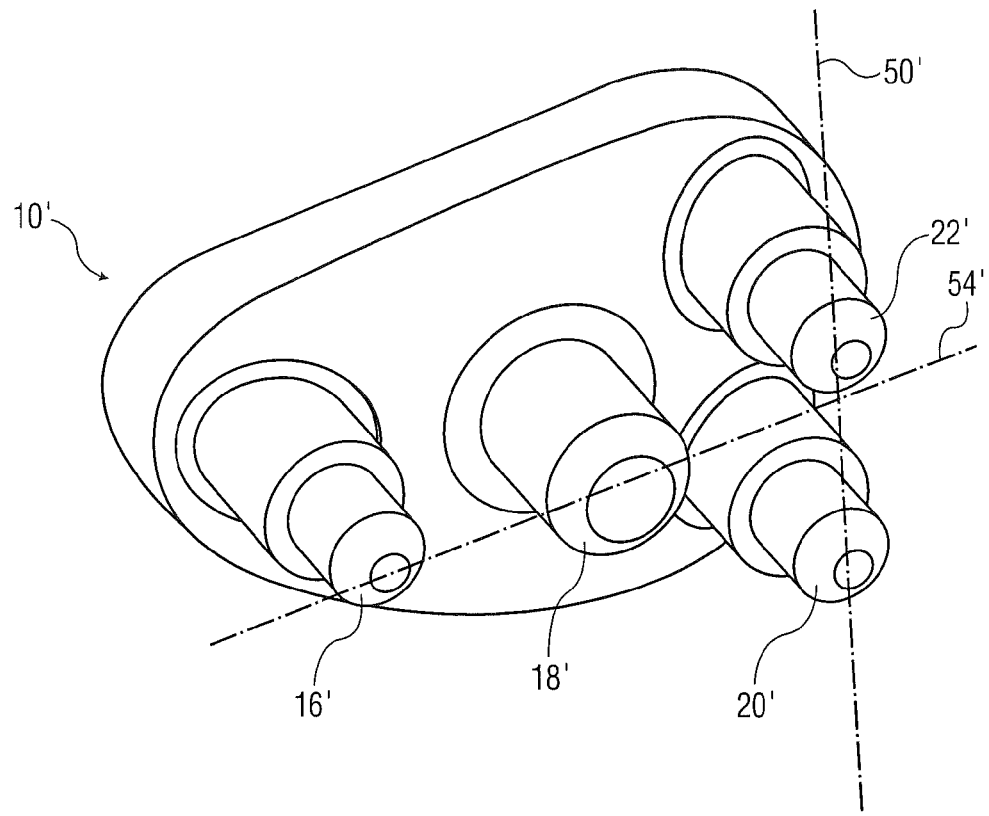
FIG. 3 is a isometric view as seen from the medial bone contacting side of an alternate embodiment of a glenoid component designed for use without bone cement.
Figure 4:
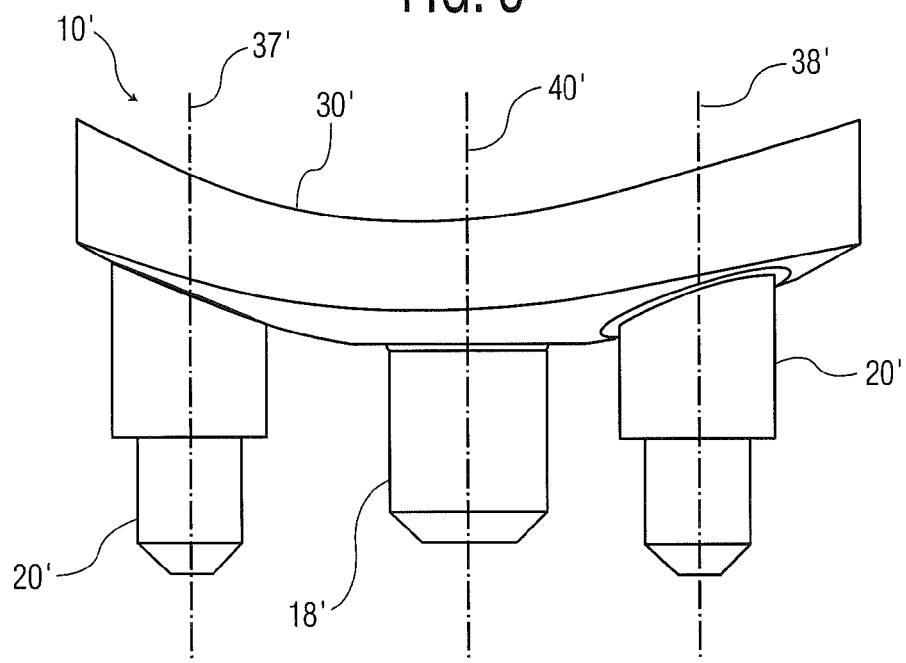
FIG. 4 is an elevation view of the alternate embodiment of FIG. 3.

Referring to FIGS. 3 and 4, there is shown an alternate glenoid component generally denoted as 10', which is in all ways similar to the glenoid component 10 of FIGS. 1 and 2 with the exception that the four pegs 16', 18', 20', and 22' have smooth or nongrooved outer surfaces. These nongrooved outer surfaces are used in press fit applications wherein the outer diameter of the pegs is equal to or very slightly more than the diameters of the corresponding bores drilled in the glenoid cavity.

As can be seen in FIGS. 1 and 3, in a preferred embodiment, a plane connecting the central axes 37, 37' of pegs 16, 16', and axis 40, 40' of pegs 18, 18' lie in a single plane 54, 54'. Likewise, pegs 20, 20' and 22, 22' have their central longitudinal axes 38 and 38' extending parallel and lying in the plane 50, 50'. Preferably, planes 54, 54' and 50, 50' are perpendicular to one another.

Figure 5:
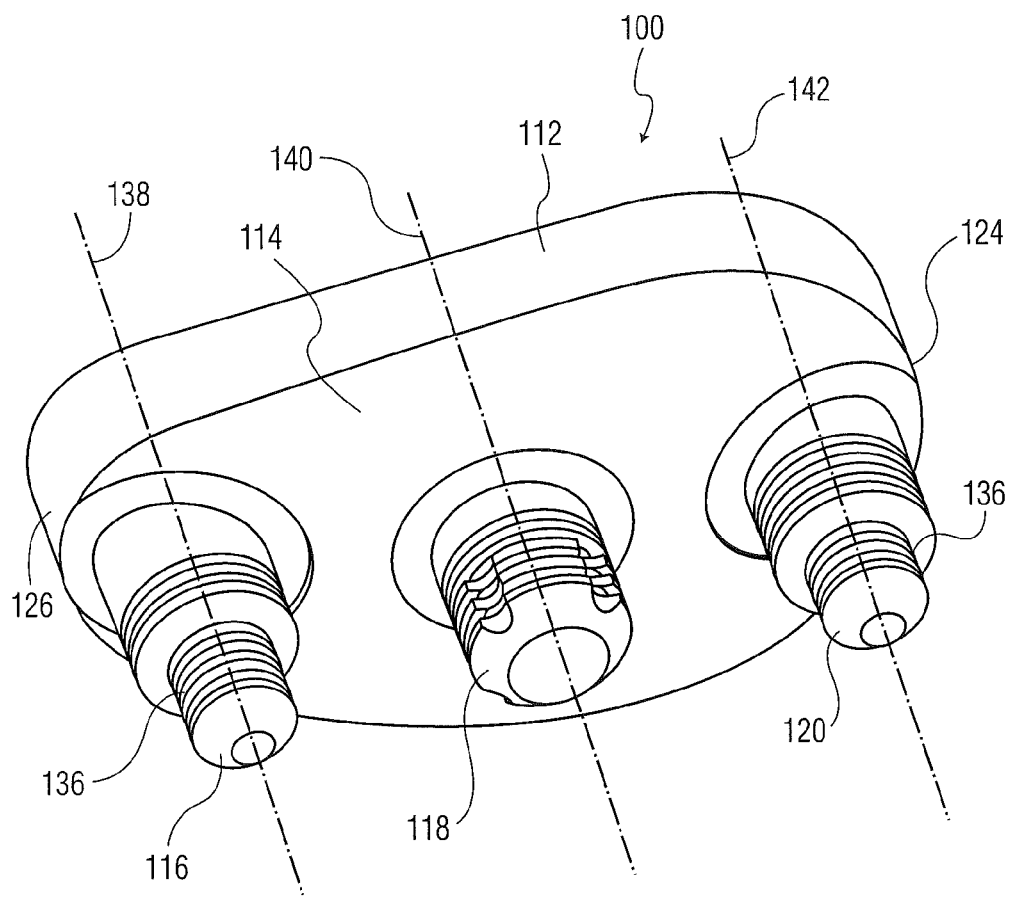
FIG. 5 is an isometric view of an additional alternate glenoid component having three pegs viewed from a medial or bone contacting side thereof.
Figure 6:
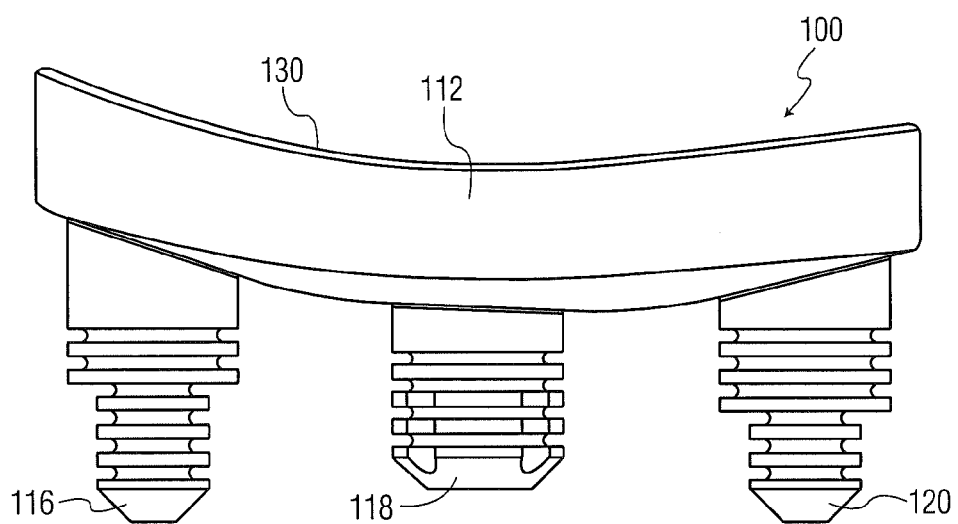
FIG. 6 is an elevation view of the glenoid component of FIG. 5.

Referring to FIGS. 5 and 6, there is shown an alternate glenoid component 100 in which a body 112 which is identical to the glenoid component of FIGS. 1-4 with the exception that there are three pegs 116, 118, and 120 extending from bone contacting surface 114. It can be seen that the bone contacting surfaces 14 and 114 are both convex in shape to match the anatomy of the glenoid cavity. The glenoid 100 of FIGS. 5 and 6 is designed to be utilized with bone cement in a manner similar to that shown in FIGS. 1 and 2 and include circumferential grooves 136 separated by flanges 144, which are identical to the grooves 36, 39 discussed above with regard to FIGS. 1 and 2. Thus, the only difference being distal end 124 and proximal end 126 include only a single peg 116 and 120. As with pegs 16 and 18, pegs 116, 118, and 136 include parallel longitudinal axes 138, 140, and 142, which lie in the same plane extending from end 124 to 126. As with the design of FIGS. 1-4, the glenoid components respectively include bearing surfaces 30, 30', and 130.

Figure 7:
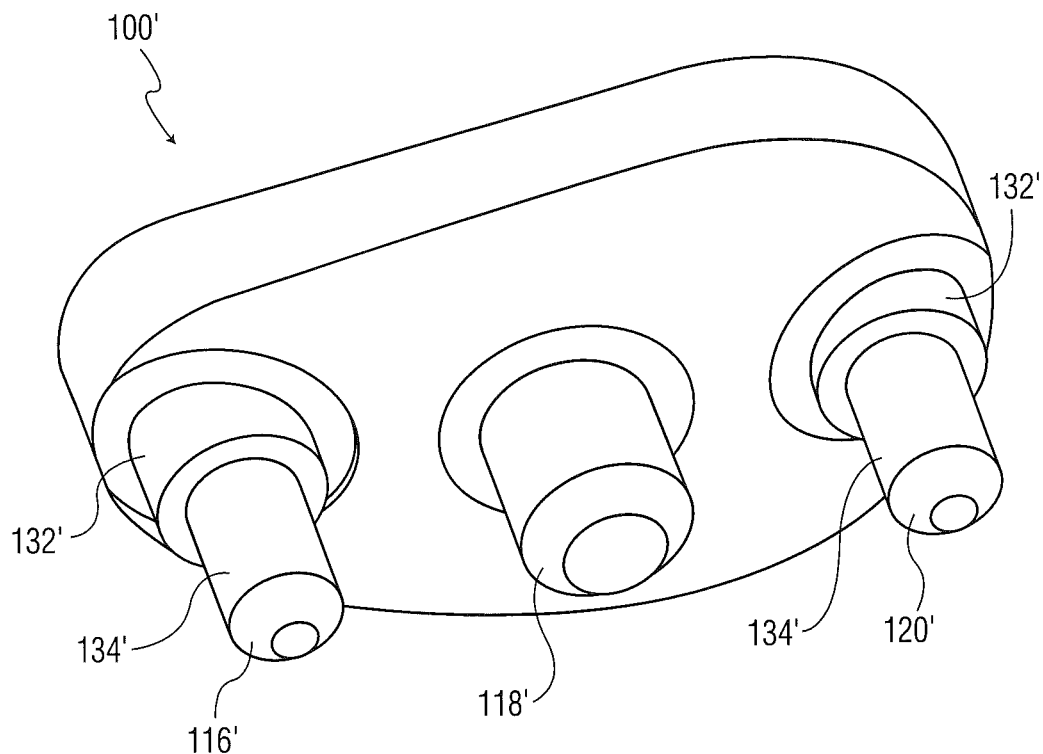
FIG. 7 is an embodiment of the glenoid component having three pegs designed for use without bone cement as seen from the bone contacting or medial side.
Figure 8:
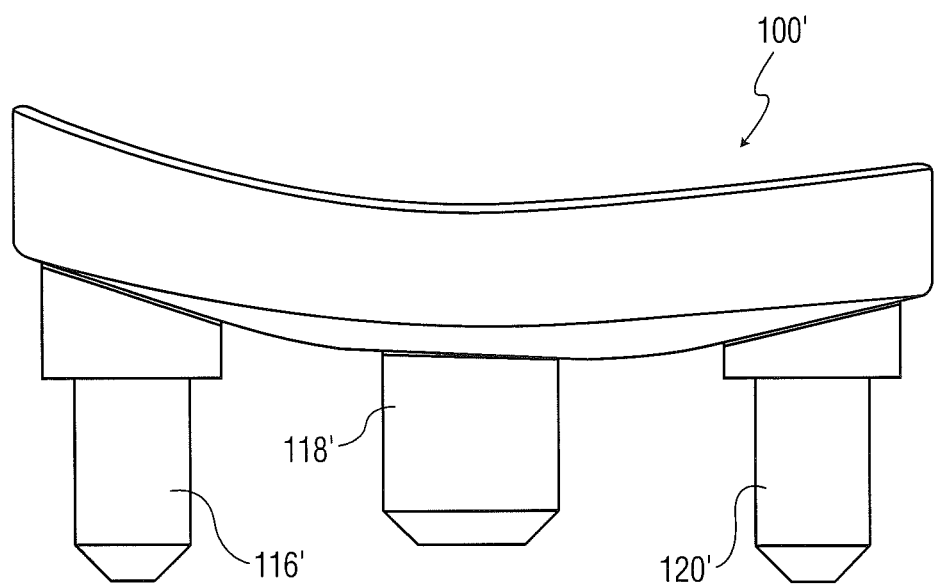
FIG. 8 is an elevation view of the glenoid component of FIG. 7.

Referring to FIGS. 7 and 8, there is shown an alternate embodiment of the glenoid component 100 of FIGS. 5 and 6 generally denoted as 100'. Like the glenoid component of FIGS. 3 and 4, the glenoid component of FIGS. 7 and 8 include smooth outer surfaces for enlarged diameter portion 132' and smaller diameter portion 134' of pegs 116' and 120' and a smooth outer surface for central peg 118'.

All of the glenoid component pegs of FIGS. 1-8, as shown specifically referring to only FIG. 1, include a portion 60 surrounded by chamfered portion 64 and, with regard to central peg 18, an enlarged portion 62 surrounded again by chamfered portion 66. The chamfered portions 64, 66 make it easier to insert the peg tips into the bores formed in the scapula.

Figure 9:
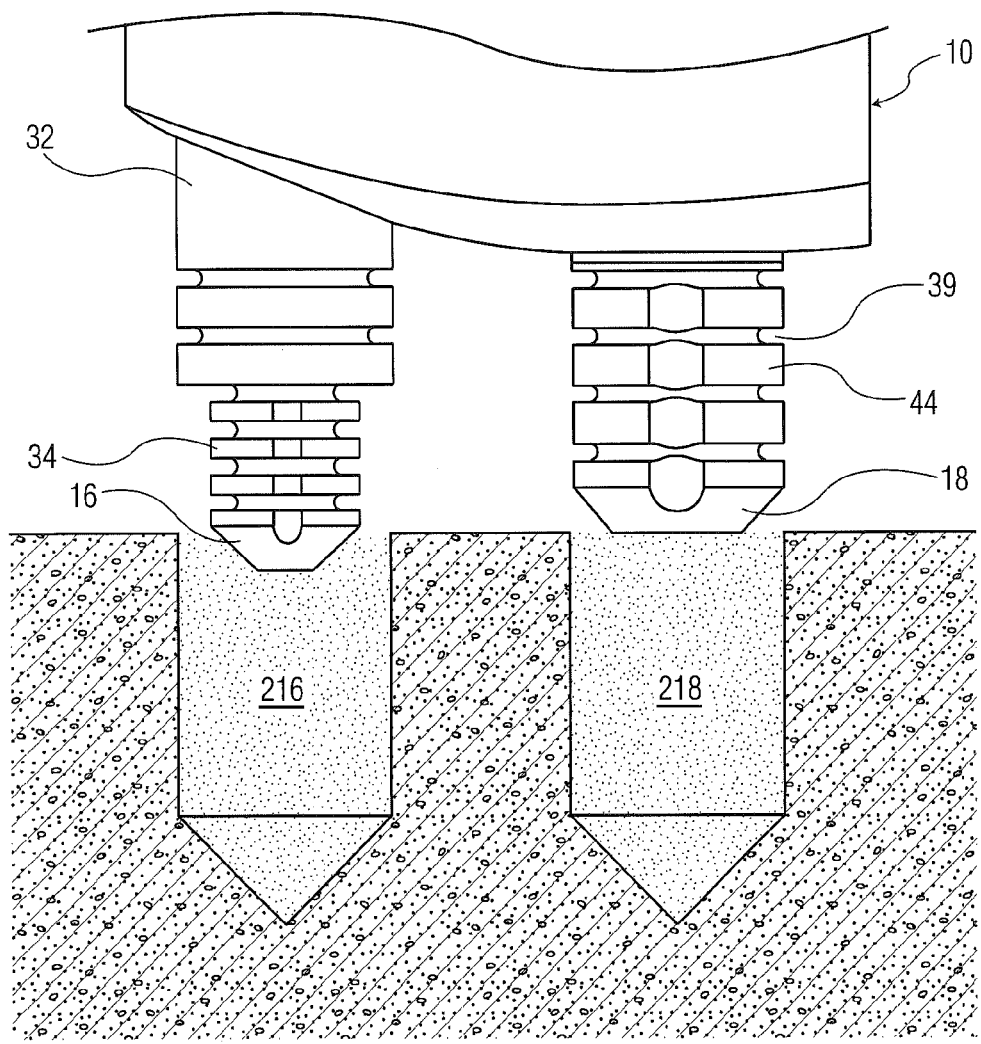
FIG. 9-11 show the method of implantation of the glenoid component of FIG. 1, using bone cement with FIG. 9 showing the location of the pegs in relation to bone cement filled bores in the scapula prior to insertion.
Figure 10:
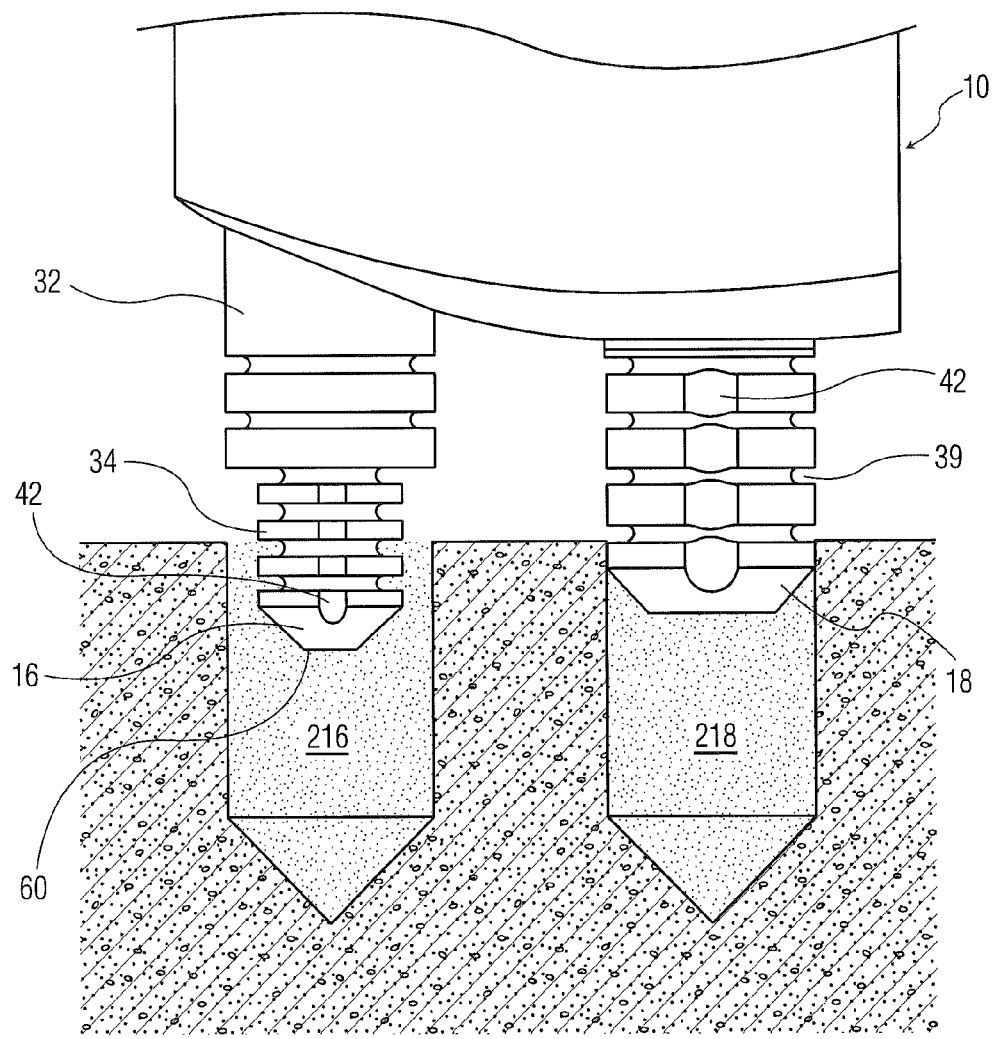
Figure 11:
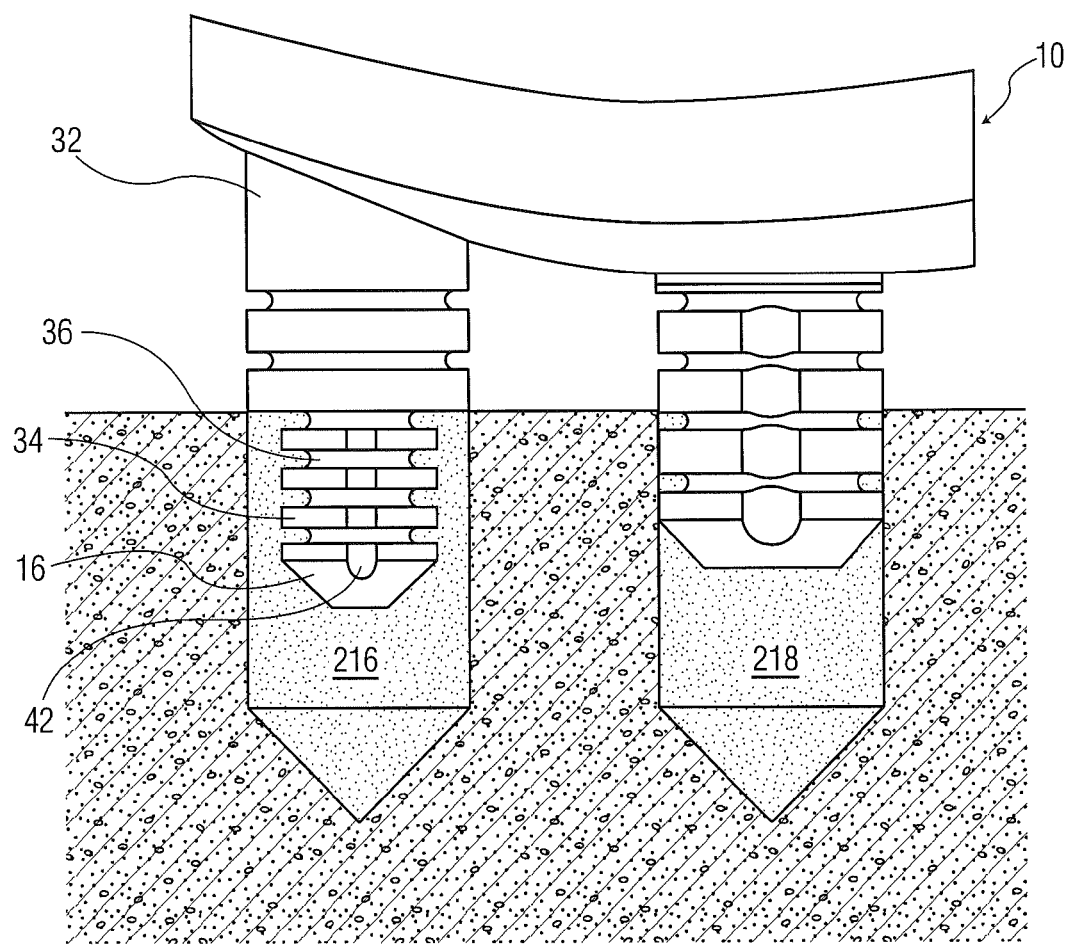

Referring to FIGS. 9-11, the insertion process of any of the glenoid components of FIGS. 1-8 will now be described. Although a glenoid component similar to those shown in FIGS. 1 and 2 and 5 and 6 is shown, the insertion technique would be the same whether a cemented or noncemented component is utilized. Again, this process will be described with reference to the glenoid component of FIGS. 1 and 2 for simplification.

Referring to FIG. 9, the glenoid component 10 is aligned over the bores in the scapula by partially inserting smaller diameter section 34 of proximal or superior peg 16 into a corresponding bore 216 and, although not shown, the reduced diameter portion 34 of distal or inferior pegs 20 and 22 in corresponding bores (not shown) on the distal side of the glenoid cavity. The partial engagement of the three reduced diameter sections 34 and their corresponding bores helps align central peg 18 with a corresponding bore 218 formed in the glenoid cavity. If a cemented implantation is used, the bores 216, 218 will have been previously filled with bone cement in a noncured state.

As shown in FIG. 10, the central peg 18 will then be partially inserted into bore 218 to center the glenoid component with respect to all the pegs and bores formed in the glenoid cavity. It will be noted that the outer diameter of peg 18 contacts the bore prior to the larger diameter portion 32 of pegs 16, 20 and 22. Also note that bone cement filling bore 218 can flow axially through groove 42 into the plurality of grooves 39 of central peg 18.

As shown in FIG. 11, further movement of the glenoid component 10 now causes large diameter portion 32 to enter bore 216 and pressurize the bone cement therein. As component 10 is moved further medially into bores 216, 218, the other bores (not shown) glenoid component 10 becomes fully seated on the scapula and is held in position until the bone cement hardens.

Since the glenoid component is typically made of UHW-MPE, when the embodiments of FIGS. 3, 4 and 7 and 8 are utilized, it is possible to form the pegs slightly larger than the bores in the scapula produce a slight interference or press fit. In this situation, bone cement is not utilized. Alternately, the grooved designs of FIGS. 1 and 2 and 5 and 6 can be utilized in a press fit manner with bone growth materials, such as calcium phosphates, packed into the grooves.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic glenoid component comprising:
a body having a concave bearing surface and a glenoid contacting surface,
a first peg extending outwardly from the glenoid contacting surface of the body, the first peg having a first length from the glenoid contacting surface to a free end of the peg, a first portion of the first length with a first maximum diameter at the glenoid contacting surface extending for a second length and a second portion with a second maximum diameter extending from the first portion for a third length to the free end of the first peg, the first maximum diameter larger than the second maximum diameter;
a second peg extending outwardly from the glenoid contacting surface, the second peg having a fourth length from the glenoid contacting surface to a free end of the second peg and a first portion of the fourth length with a first maximum diameter and a second portion of the fourth length with a second maximum diameter, the first maximum diameter being larger than the second maximum diameter of the second peg, the second portion of the second peg extending to the free end of the second a third peg extending outwardly from the glenoid contacting surface intermediate the first and second pegs, the third peg having a third maximum diameter greater than the second maximum diameter of the first peg second portion and a fifth length greater than the second length of the first peg portion, the fifth length less than the first and fourth lengths of the first and second pegs respectively.

2. The prosthetic glenoid component as set forth in claim 1, wherein the maximum diameters of the first peg first and second portions are equal to the maximum diameters of the respective second peg first and second portions.

3. The prosthetic glenoid component as set forth in claim 1, wherein the first and second pegs each have circumferential grooves formed on their first and second maximum diameters.

4. The prosthetic glenoid component as set forth in claim 3, wherein the first and second peg maximum diameters have longitudinally extending grooves.

5. The prosthetic glenoid component as set forth in claim 1, wherein the first, second, and third pegs each have a longitudinal central axis wherein the longitudinal axis of the first, second, and third pegs are all parallel.

6. The prosthetic glenoid component as set forth in claim 1, wherein the first maximum diameter of first portion of the the first and second pegs is equal to the third maximum diameter of the third peg.

7. The prosthetic glenoid component as set forth in claim 1 further comprising a fourth peg extending outwardly of the gleonid contacting surface adjacent a distal end of the bone contacting surface.

8. The glenoid component as set forth in claim 7, wherein the fourth peg has a first and second portion identical to the first and second portions of the first peg.

9. The glenoid component as set forth in claim 7, wherein the first and fourth pegs have central longitudinal axes which are parallel and coplanar along a first plane.

10. The glenoid component as set forth in claim 9, wherein the second and third pegs have central longitudinal axes which are parallel and coplanar along a second plane which is perpendicular to the first plane.

11. The glenoid component as set forth in claim 7, wherein the first and fourth pegs have central longitudinal axes which are parallel and coplanar.

12. The glenoid component as set forth in claim 10, wherein the central axis of the second peg is parallel and coplanar with the central axis of the third peg.

13. A prosthetic glenoid component comprising:
a body having a concave bearing surface and a glenoid contacting surface,
a first peg extending outwardly from the glenoid contacting surface of the body, the first peg having a first portion with a first maximum diameter at the glenoid contacting surface extending for a first length and a second portion with a second maximum diameter extending from the first portion to a free end of the first peg for a second length, the first maximum diameter larger than the second maximum diameter,
a second peg extending outwardly from the glenoid contacting surface, the second peg having a third length, the second peg having a first portion with a first maximum diameter and a second portion with a second maximum diameter, the first maximum diameter of the second peg being larger than the second maximum diameter of the second peg, a third peg extending outwardly from the glenoid contacting surface intermediate the first and second pegs, the third peg having a third maximum diameter greater than the second maximum diameter of the first peg second portion and a fourth length greater than the first length of the first peg first portion, the fourth length less than the sum of the lengths of the first and second first peg portions; and a fourth peg extending outwardly from the glenoid contacting surface adjacent a distal end of the body having the glenoid contacting surface.

14. The prosthetic glenoid component as set forth in claim 13, wherein the first and second maximum diameters of the first peg are equal to the respective first and second maximum diameters of the second peg.

15. The prosthetic glenoid component as set forth in claim 13, wherein the first and second pegs each have circumferential grooves formed around the first and second portions.

16. The prosthetic glenoid component as set forth in claim 15, wherein the first and second portions of the first and second pegs have longitudinally extending grooves open to the maximum diameters.

17. The prosthetic glenoid component as set forth in claim 13, wherein the first, second, third and fourth pegs each have a longitudinal central axis wherein the longitudinal central axis of the first, second, third and fourth pegs are all parallel.

18. The prosthetic glenoid component as set forth in claim 17 wherein the longitudinal central axes of the first and fourth pegs are coplanar.

* * * * *

UNITED STATES PATENT AND TRADEMARK OFFICE
CERTIFICATE OF CORRECTION

PATENT NO. : 8,876,907 B2
APPLICATION NO. : 13/558872
DATED : November 4, 2014
INVENTOR(S) : Alexandre A. N. Baptista et al.

Page 1 of 1

It is certified that error appears in the above-identified patent and that said Letters Patent is hereby corrected as shown below:

In The Specification

Column 6, line 7, after "end of the second" insert --peg; and--

Signed and Sealed this
Second Day of August, 2016

Michelle K. Lee
*Director of the United States Patent and Trademark Office*